United States Patent
Alchenberger et al.

(10) Patent No.: US 10,315,976 B2
(45) Date of Patent: *Jun. 11, 2019

(54) ORGANIC COMPOUNDS

(71) Applicant: Givaudan SA, Vernier (CH)

(72) Inventors: Alain Alchenberger, Zurich (CH);
Chloe Berbez, Argenteuil (FR); Clare Finn, Paris (FR); Dominique Lelievre, Kindhausen (CH); Martin Alan Lovchik, Dübendorf (CH); Roseline Poignon-Martel, Argenteuil (FR); Gilles Romey, Argenteuil (FR)

(73) Assignee: GIVAUDAN S.A., Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/212,864

(22) Filed: Jul. 18, 2016

(65) Prior Publication Data

US 2016/0326082 A1  Nov. 10, 2016

Related U.S. Application Data

(63) Continuation of application No. 14/651,719, filed as application No. PCT/EP2014/062002 on Jun. 10, 2014, now Pat. No. 9,469,590.

(30) Foreign Application Priority Data

Jan. 10, 2013 (EP) .................................. 13290129

(51) Int. Cl.
| | | |
|---|---|---|
| *A61K 8/00* | (2006.01) | |
| *C07C 47/263* | (2006.01) | |
| *C07C 29/17* | (2006.01) | |
| *C07C 45/82* | (2006.01) | |
| *C07C 29/04* | (2006.01) | |
| *C11B 9/00* | (2006.01) | |
| *C07C 45/51* | (2006.01) | |
| *A61K 8/33* | (2006.01) | |
| *A61K 8/34* | (2006.01) | |
| *A61Q 5/02* | (2006.01) | |
| *A61Q 19/10* | (2006.01) | |
| *C11D 3/20* | (2006.01) | |
| *C11D 3/50* | (2006.01) | |
| *A61K 8/40* | (2006.01) | |
| *A61K 8/49* | (2006.01) | |
| *C11D 3/00* | (2006.01) | |
| *C11D 11/00* | (2006.01) | |

(52) U.S. Cl.
CPC ............. *C07C 47/263* (2013.01); *A61K 8/33* (2013.01); *A61K 8/342* (2013.01); *A61K 8/40* (2013.01); *A61K 8/498* (2013.01); *A61Q 5/02* (2013.01); *A61Q 19/10* (2013.01); *C07C 29/04* (2013.01); *C07C 29/17* (2013.01); *C07C 45/515* (2013.01); *C07C 45/82* (2013.01); *C11B 9/008* (2013.01); *C11B 9/0015* (2013.01); *C11B 9/0023* (2013.01); *C11B 9/0042* (2013.01); *C11B 9/0065* (2013.01); *C11D 3/001* (2013.01); *C11D 3/2072* (2013.01); *C11D 3/50* (2013.01); *C11D 11/0017* (2013.01); *C07B 2200/09* (2013.01)

(58) Field of Classification Search
CPC .................................................... C11B 9/0015
See application file for complete search history.

(56) References Cited

U.S. PATENT DOCUMENTS

| | | |
|---|---|---|
| 3,953,518 A | 4/1976 | Wehrli |
| 4,057,515 A | 11/1977 | Boelens et al. |
| 4,271,048 A | 6/1981 | Buechi et al. |
| 5,155,095 A | 10/1992 | Blanc et al. |
| 6,017,907 A | 1/2000 | Bouillon et al. |
| 9,469,590 B2 * | 10/2016 | Alchenberger ......... C07C 45/82 |

FOREIGN PATENT DOCUMENTS

| | | |
|---|---|---|
| GB | 981702 A | 1/1965 |
| GB | 981702 A2 | 1/1965 |
| GB | 1158791 | 7/1969 |
| GB | 1414759 | 11/1975 |
| GB | 2515128 A | 12/2014 |
| JP | 5291815 A | 8/1977 |
| WO | 9519963 A1 | 7/1995 |
| WO | 9852894 A1 | 11/1998 |
| WO | 2008087609 A2 | 7/2008 |
| WO | 2014198709 A1 | 12/2014 |
| WO | 2015181257 A2 | 12/2015 |

OTHER PUBLICATIONS

International Search Report for PCT/EP2014/062002 dated Aug. 4, 2014.
Written Opinion of the international Searching Authority for PCT/EP2014/062002 dated Aug. 4, 2014.
GB Search Report for GB 1313641.1 dated Jan. 29, 2014.
Anonymous, "Opinion of the Scientific Committee on Cosmetic Products and Non-Food Products Intended for Consumers Concerning Hydroxyisohexyl 3-Cyclohexene Carboxaldehyde", Dec. 2003, XP002726813, retrieved from the Internet, URL: http://ec.europa.eu/health/archive/ph_risk/committees/sccp/documents/out249_en.pdf.
International Search Report and Written Opinion of the International Searching Authority for corresponding application PCT/EP2015/079017 dated Mar. 9, 2016.

(Continued)

*Primary Examiner* — John R Hardee
(74) *Attorney, Agent, or Firm* — Norris McLaughlin PA

(57) ABSTRACT

5,9-dimethyl-9-hydroxy-decen-4-al, having the formula (I)

(I)

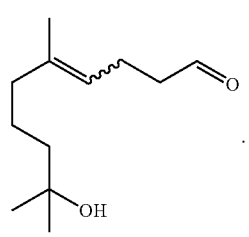

19 Claims, No Drawings

(56) References Cited

OTHER PUBLICATIONS

GB Search Report for corresponding application GB1421838.2 dated Sep. 15, 2015.
International Search Report and Written Opinion of the International Searching Authority for corresponding application PCT/EP2015/079009 dated Feb. 3, 2016.
GB Search Report for corresponding application GB1421855.6 dated Sep. 15, 2015.
Bestmann, et al., "New Synthesis of Macrocyclic lactones", Angewandte Chemie, vol. 95, pp. 810-811, 1983.
Bestmann, et al., Synthesis, vol. 6, pp. 419-423, 1989.
Kutner, et al., "Synthesis of Retiferol RAD1 and RAD2, the Lead Representitives of a New Class of des-CD od Cholecalciferol1", Bioorganic Chemistry, vol. 23(1), 1995, pp. 22-32.
Plonska-Ocypa, et al., "Synthesis and biological evaluation of a des-C, D-analog of 2 methylene-19-nor-1alpha,25-(OH)2D3", Journal of Steroid Biochemistry and Molecular Biology, Elsevier Science Ltd., vol. 103, No. 3-5, pp. 298-304, Oxford, GB, Mar. 2007.

* cited by examiner

ORGANIC COMPOUNDS

This is a divisional patent application of U.S. Ser. No. 14/651,719, now U.S. Pat. No. 9,469,590 which in turn was filed as a 35 USC 371 application of PCT/EP2014/062002, filed 10 Jun. 2014, which claims priority benefit to EP 13290129.9 filed 10 Jun. 2013. The present application claims the full priority benefit of the foregoing applications, and also herein incorporates by reference their entire disclosures as if set forth herein.

This invention relates to a novel compound, a method of preparing the compound, and its use as a fragrance ingredient, in particular its use as a fragrance ingredient to impart a muguet odour characteristic to a perfume composition. The invention also relates to perfume compositions and to articles, such as fine fragrances or consumer product compositions perfumed by the compound, or the perfume compositions containing said compound.

Compounds having muguet (or lily of the valley) odour characteristics are very sought after as perfume ingredients. These compounds are important ingredients in floral bases and can act as harmonizers across many types of fragrance creations. Compounds of this type are used widely in personal care and consumer care products, as well as in fine perfumery, to generate pleasant odours or to mask unpleasant odours.

An excellent perfume ingredient widely valued for its muguet odour note is 4(4-hydroxy-4-methylpentyl) 3-cyclohexene carboxaldehyde, otherwise known as cyclohexal (Lyral™) This compound has found wide use in fine perfumery as well as in personal and household care products. However according to findings of the European Scientific Committee for Consumer Safety (SCCS) it has allergenic concerns and at the present time may be subject to regulatory action in the EU.

The problem addressed by the present invention is to provide new ingredients and new perfume preparations, in particular, which are perceived and recognised by perfumers as having substantially the same odour characteristics as cyclohexal, as well as having similar or even improved perfume performance compared to cyclohexal.

Accordingly, the invention provides in a first aspect the compound 5,9-dimethyl-9-hydroxy-decen-4-al, having the formula (I)

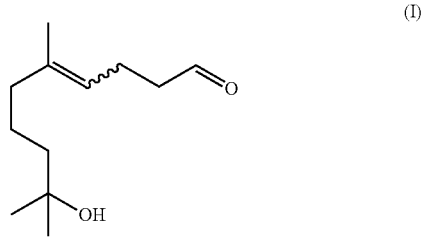

(I)

The compound according to the present invention was found by the applicant to have a classic floral, green muguet odour note that was reminiscent of cyclohexal. Accordingly, 5,9-dimethyl-9-hydroxy-decen-4-al could be an eminently suitable replacement for cyclohexal.

A process of preparing γ,δ-unsaturated aldehydes and ketones is disclosed in GB 981,702. This patent generally describes the reaction of allylic alcohols with enol ethers, followed by a rearrangement reaction at elevated temperature. In an attempt to demonstrate the scope of the synthetic procedure, examples are provided using a variety of allylic alcohols bearing different functionality. The examples include allylic alcohols bearing saturated and unsaturated alkyl groups, cycloalkanes, double bonds, aromatic rings, as well as oxygen containing functionality, such as hydroxyl groups.

In Example 27 of GB 981,702, it purports to describe a method of preparing the compound 5,9-dimethyl-9-hydroxy-decen-4-al starting from the hydroxyl-substituted allylic alcohol substrate, hydroxylinalool.

The reaction proceeds by mixing hydroxy linalool with vinyl ethyl ether in phosphoric acid. This organic mixture is worked-up in base and distilled, before the distillate is added to an aqueous solution of sodium bisulphite and the organic layer is discarded. The aqueous phase is then treated with 30% sodium hydroxide before being extracted with ether. The aqueous layer is discarded and the ethereal layer is treated with bicarbonate. After evaporation of the ether, the crude product is distilled to isolate the final product. The final product was characterised by its odour characteristics, as well as its boiling point and refractive index.

The isolated final product was described as having a "pleasantly fruity and smoky-fatty odour". This finding was curious in view of the applicant's own finding that the target compound 5,9-dimethyl-9-hydroxy-decen-4-al actually exhibits a classical muguet odour, which is completely unrelated to the odour reported in GB 981,702. Furthermore, the boiling point and refractive index measurements of the compound 5,9-dimethyl-9-hydroxy-decen-4-al, as measured by the applicant, differs markedly from the product obtained according to the process of this Example 27. Specifically, the product obtained in Example 27 had a reported boiling point of 83-85° C./0.03 mm and a refractive index $n_D^{20}$ of 1.4698. In fact, the true values for 5,9-dimethyl-9-hydroxy-decen-4-al were found by the applicant to be 106-109° C./0.05 mm, and $n_D^{20}$ of 1.4659.

When the applicant reproduced the synthetic conditions described in Example 27 it was not possible to recover any 5,9-dimethyl-9-hydroxy-decen-4-al. In fact, what was recovered, after removing a large amount of polymeric residue was an isomeric mixture of the compound:

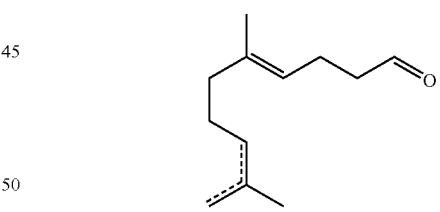

Upon analysis, this compound was found to have a boiling point of 85° C. at 0.03 mm and an $N_D^{20}$ of 1.4682. Furthermore, the odour characteristics were described by perfumers to be fruity, citrus, fatty, slightly hot iron and metallic. Conspicuously, these parameters showed remarkable conformance with those disclosed for the isolated final product of GB 981,702, Example 27.

From the foregoing, it is quite apparent that GB 981,702 does not constitute an enabling disclosure regarding the compound 5,9-dimethyl-9-hydroxy-decen-4-al, or its preparation. Indeed, what the authors of GB 981,702 did not appreciate, and what the applicant has found after considerable research effort into this reaction, is that the introduction of a hydroxyl substituent in the allylic alcohol starting material (as in the case of hydroxylinalool of Example 27, which is the only example of the use of a hydroxyl-substituted allylic alcohol starting material), greatly changes the stability and chemical properties of the product. The use of sulphite adducts as a means of separating aldehydes from complex mixtures is a known technique used by the authors of GB981,702, however, liberation of the final product from the adduct is achieved by hydrolysis in strong base (30% sodium hydroxide), as well as subsequent treatment with strong acid and this causes undesirable side reactions.

Applicant surprisingly discovered that 5,9-dimethyl-9-hydroxy-decen-4-al is both thermally unstable, and unstable in alkaline media, therefore gentle reaction and isolation conditions are required if it is to be successfully prepared.

Accordingly, in another aspect of the present invention there is provided a method of preparing 5,9-dimethyl-9-hydroxy-decen-4-al (I) from a reaction mixture, comprising the step of presenting the reaction mixture in a form substantially free of any acid or base, and distilling the mixture 5,9-dimethyl-9-hydroxy-decen-4-al from the reaction mixture.

In a particular embodiment of the present invention the reaction mixture may be presented in a form substantially free of acid or base if it is neutralised with an aqueous washing liquor, which may be one or more of water, optionally containing a salt, such as sodium chloride, an aqueous solution of an acid or an aqueous solution of a base.

The acid may be selected from the group consisting of C-1 to C4 carboxylic acids, such as acetic acid, polycarboxylic acids such as citric acid and weak mineral acids.

The base may be selected from the group consisting of a weak base, such as sodium or potassium (hydrogen) carbonate.

The reaction mixture is deemed to be substantially free of acid or base when after washing, the washing liquor has a pH of between about 6.5 to about 7.5.

The applicant found that in alkaline conditions above pH 10, or in acidic conditions below about pH 4, 5,9-dimethyl-9-hydroxy-decen-4-al is rapidly degraded at ambient temperature, and the degradation proceeds even more rapidly at elevated temperatures. Accordingly, if the object of preparing and isolating 5,9-dimethyl-9-hydroxy-decen-4-al is to be achieved, it should not be subjected to alkaline conditions, of if alkaline conditions are encountered, they should not be above 10, more particularly above 9.5, and still more particularly above 9. Strong bases, such as sodium hydroxide should be avoided, preferably, although if used, care should be taken that the pH does not rise to the aforementioned values. And furthermore, when distilling 5,9-dimethyl-9-hydroxy-decen-4-al in order to present it in olfactively pure form, it should be first ensured that the reaction mixture containing it is substantially free of acid or base, as stated herein above.

Distillation may be carried out at a temperature of 95° C. to 200° C. and at a pressure of 0.01 mm to 10 mm, more particularly 0.01 mm to 5 mm.

Due to the thermal sensitivity of 5,9-dimethyl-9-hydroxy-decen-4-al, it may be desirable if the distillation step is shortened in duration as much as possible. In order to simplify the distillation process and to shorten the duration, one can first separate 5,9-dimethyl-9-hydroxy-decen-4-al from organic by-products of the reaction mixture by treating 5,9-dimethyl-9-hydroxy-decen-4-al with aqueous sodium metabisulphite to form the sulphonate of 5,9-dimethyl-9-hydroxy-decen-4-al, which is soluble in the aqueous phase. The sulphonate of the following formula forms another aspect of the present invention.

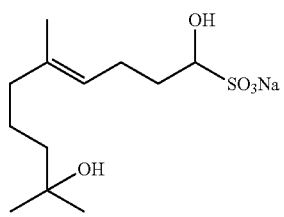

Thereafter, an organic solvent, can be added to the aqueous phase and 5,9-dimethyl-9-hydroxy-decen-4-al can be regenerated by treating the sulphonate with a dilute solution of a weak base, for example sodium carbonate. Once regenerated, 5,9-dimethyl-9-hydroxy-decen-4-al partitions into the organic phase, and this phase is washed with dilute weak acid to remove traces of base, before distillation is undertaken.

5,9-dimethyl-9-hydroxy-decen-4-al may be prepared from an allylic alcohol precursor. This precursor may be linalool, or a hydroxyl-substituted allylic alcohol, such as hydroxylinalool. Still further, it could be a hydroxyl-substituted allylic alcohol, wherein the non-allylic hydroxyl substituent is in a protected or masked form, such as its acetate.

The allylic alcohol precursor is converted to 5,9-dimethyl-9-hydroxy-decen-4-al by carrying out a Claisen Rearrangement reaction in the presence of an acid, which is a technique well known to a skilled person in the art. The acid is employed to first effect a trans-etherification on the allylic hydroxyl group, and it is the ether that is formed, which undergoes the rearrangement reaction, as is well known in the art.

The allylic alcohol precursor has the following formula:

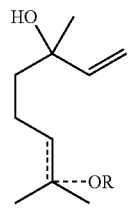

wherein,
═ is a double bond or a single bond, and
-----OR is a hydroxyl group or a protected hydroxyl group, such as an acetate, silyl ether or mixed acetal, provided that -----OR is present only when ═ is a single bond.

In a preferred embodiment of the present invention, the precursor is hydroxy linalool, however, a protected form of hydroxy linalool, e.g. the acetate, might also be employed.

If the precursor contains the group ═ as a double bond, once the Claisen Rearrangement is carried out, that double bond can be hydrolysed to add a hydroxyl group and release the desired 5,9-dimethyl-9-hydroxy-decen-4-al, according to techniques known to a person skilled in the art. Thereafter, steps are taken to ensure the reaction mixture contains substantially no acid or base before being subjected to distillation, as described hereinabove.

The allylic alcohol precursors are either commercially available, or can be prepared from commonly available starting materials using techniques known to the person skilled in the art.

The Claisen Rearrangement reaction occurs readily when a vinyl ether is reacted with an allylic alcohol precursor, in the presence of an acid or metal catalyst, at a temperature in a range spanning ambient to about 200° C. Typically, the reaction is carried out at high pressure in an autoclave. Any desired pressure above atmospheric can be employed in an autoclave, for example, up to 100 bar, and more particularly about 5 to 20 bar.

The applicant has found, however, that the reaction can be carried out at atmospheric pressure, in an unpressurised reaction vessel, when employing diethyleneglycol divinylether or triethyleneglycol divinyl ether, as the vinyl ether.

Optionally, the reaction is carried out under an inert atmosphere, for example under a nitrogen atmosphere.

Once the rearrangement reaction is complete, the reaction mixture can be treated with acid to hydrolyze any acetals that are formed during the course of the reaction.

In a particular embodiment of the present invention there is provided a method of preparing 5,9-dimethyl-9-hydroxy-decen-4-al (I), comprising the steps of reacting an allylic alcohol precursor, preferably hydroxy linalool, with diethyleneglycol divinylether in the presence of an acid under an inert gas atmosphere, at atmospheric pressure and a temperature of 125 to 200° C.; treating the reaction mixture containing 5,9-dimethyl-9-hydroxy-decen-4-al with dilute acid to hydrolyse substantially all acetals; and remove substantially all acids and bases, before subjecting the neutralised reaction mixture to distillation in a manner described above.

In another aspect of the present invention there is provided a method of preparing 5,9-dimethyl-9-hydroxy-decen-4-al (I), said method comprising the steps of:

I) reacting hydroxylinalool (3) with ethyl vinyl ether in acid under an inert gas atmosphere at 1 to 100 bar, more specifically at 5-20 bar and a temperature of −10 to 200 degrees centigrade, more specifically at 140-190 degrees centigrade to form a reaction mixture comprising acetals;

II) acidifying the cooled reaction mixture at −20 to 40 degrees centigrade and atmospheric pressure to hydrolyse said acetals;

III) neutralising the reaction mixture in a base before adjusting the pH of the reaction mixture to a slightly acidic pH of 4 to 6, to yield 5,9-dimethyl-9-hydroxy-decen-4-al (I); and IV) distilling the reaction mixture to isolate pure 5,9-dimethyl-9-hydroxy-decen-4-al (I).

The rearrangement reaction described above, for example, the reaction of hydroxylinalool (3) with ethyl vinyl ether described above, proceeds under acidic conditions. Particular acids useful in the present invention include phenyl phosphonic acid, sulfosalicylic acid, phosphoric acid buffered with various amounts of amines, phosphoric acid, ammonium salts, alkyl carboxylic acids and aryl carboxylic acids.

Whereas hydroxylinalool (3) is a commonly available starting material, it can be formed in a straightforward manner starting from 3,7-dimethyloct-6-en-1-yn-3-ol (1) and hydrating this compound in aqueous sulphuric acid to afford the compound (2). Selective hydrogenation of the triple bond with a suitable catalyst, such as a palladium catalyst leads to hydroxyl linalool (3), which can be further converted to the target compound 5,9-dimethyl-9-hydroxy-decen-4-al (I) in accordance with the preparative method of the present invention. A general reaction scheme is set forth Scheme 1.

Scheme 1:

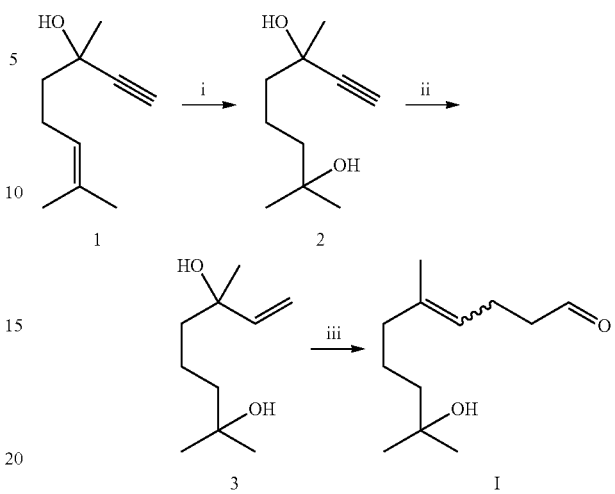

5,9-dimethyl-9-hydroxy-decen-4-al (I) can be provided in pure or enriched form in respect of its E- or Z-isomers. The strength (i.e. detection threshold) as well as the olfactive character or quality of this odourant may be affected by the relative proportions of geometric isomers contained in isomeric mixtures. If pure forms of the isomers are desired they can be obtained using synthetic procedures or by physical separation as is generally known in the art.

In a particular embodiment of the invention the E/Z ratio of 5,9-dimethyl-9-hydroxy-decen-4-al (I) is within the range of 8:2 to 2:8, or more particularly in a ratio of 6:4.

In a particular embodiment of the invention, a particularly desirable olfactive impression is obtained when 50 to 70 wt % of 5,9-dimethyl-9-hydroxy-decen-4-al is present in the E-form, and 30 to 50 wt % is in the Z-form.

The compound of formula (I) can be purified to afford its olfactively pure form, that is, a form in which there are no traces of impurity present at levels that can substantially affect odour character or quality. The applicant has found, however, that certain by-products from the reaction mixture from which 5,9-dimethyl-9-hydroxy-decen-4-al is isolated can complement the odour quality, or not adversely affect the odour quality, at least.

Accordingly, in another aspect of the invention there is provided a perfume mixture comprising 5,9-dimethyl-9-hydroxy-decen-4-al (I) and a compound according to the formula (II)

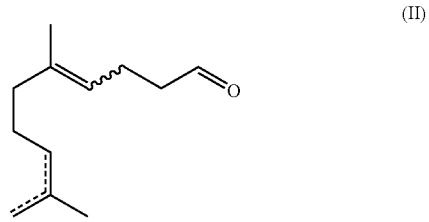

(II)

In a particular embodiment of the present invention there is provided a perfume mixture comprising 5,9-dimethyl-9-hydroxy-decen-4-al (I) and a compound according to the formula (II) in a ratio (weight/weight) that is 95 to 5 parts; more particularly 99 to 1 part, more particularly 99.1 to 0.9 parts; 99.2 to 0.8 parts; 99.3 to 0.7 parts; 99.4 to 0.6 parts; 99.5 to 0.5 parts; 99.6 to 0.4 parts; 99.7 to 0.3 parts; 99.8 to 0.2 parts; 99.9 to 0.1 parts; 99.95 to 0.05 parts; or 99.99 to 0.01 parts. The skilled person will appreciate that the compound of formula (II) may exist in pure form or may exist as a mixture of isomers. The aforementioned ratios relate to both the compound (II) in isomerically pure form or in any isomeric mixture thereof.

The compound of formula (I) and perfume mixtures referred to hereinabove were found to exhibit odour characteristics that are similar to cyclohexal, and as such can be employed in perfume compositions as a replacement for cyclohexal.

Accordingly, in another aspect of the present invention there is provided the use of a compound of formula (I), alone or in admixture with a compound (II) as a replacement for cyclohexal.

In yet another aspect of the present invention there is provided a perfume composition comprising a compound of formula (I) alone or in admixture with a compound of formula (II), and which is free of cyclohexal.

In yet another aspect of the present invention there is provided perfumed article, such as a fine fragrance or a personal or household care product, perfumed with a a compound of formula (I), optionally in admixture with a compound of formula (II).

Whereas the compound of formula (I) or the mixtures referred to above have very similar odour characteristics as cyclohexal, nevertheless a perfumer may find it desirable to employ additional perfume ingredients in combination with the compound of formula (I) or the perfume mixtures, in order to balance or fine tune the odour characteristics, for example, to bring the compound or mixtures referred to above into even closer conformance with the odour characteristics of cyclohexal.

Accordingly, in another aspect of the present invention there is provided a perfume composition comprising a compound according to formula (I), optionally in admixture with a compound of formula (II) as hereinabove described, together with one or more of the following ingredients: 2-cyclohexylidene-2-phenylacetonitrile, e.g. PEONILE™; 4-(octahydro-4,7-methano-5H-inden-5-ylidene)butanal, e.g. DUPICAL™; and 4-methyl-2-(2-methylpropyl)tetrahydro-2H-pyran-4-ol, e.g. FLOROSA™; methyl 2-(2-hexyl-3-oxocyclopentyl)acetate, e. g. HEDIONE™.

In a particular embodiment of the present invention a perfume composition comprises 2-cyclohexylidene-2-phenylacetonitrile.

In another particular embodiment of the invention, a perfume composition comprises 2-cyclohexylidene-2-phenylacetonitrile and 4-methyl-2-(2-methylpropyl)tetrahydro-2H-pyran-4-ol.

In yet another particular embodiment of the invention, a perfume composition comprises 2-cyclohexylidene-2-phenylacetonitrile and 4-Methyl-2-(2-methylpropyl)tetrahydro-2H-pyran-4-ol and 4-(octahydro-4,7-methano-5H-inden-5-ylidene)butanal.

In a perfume composition according to the present invention 2-cyclohexylidene-2-phenylacetonitrile, e.g. PEONILE™ may be employed in 0.001 to 10 parts by weight per 1 part by weight 5,9-dimethyl-9-hydroxy-decen-4-al.

In a perfume composition according to the present invention 4-methyl-2-(2-methylpropyl)tetrahydro-2H-pyran-4-ol, e.g. FLOROSA™ may be employed in 0.01 to 20 parts by weight per 1 part by weight 5,9-dimethyl-9-hydroxy-decen-4-al.

In a perfume composition according to the present invention 4-(octahydro-4,7-methano-5H-inden-5-ylidene)butanal, e.g. DUPICAL™ may be employed in 0.0001 to 0.5 parts by weight per 1 part by weight 5,9-dimethyl-9-hydroxy-decen-4-al.

In a perfume composition according to the present invention methyl 2-(2-hexyl-3-oxocyclopentyl)acetate, e. g. HEDIONE™ may be employed in 0.001 to 10 parts by weight per 1 part by weight 5,9-dimethyl-9-hydroxy-decen-4-al.

In a perfume composition, the compound of formula (I), optionally in combination with a compound (II) may be employed in an amount of about 1 to 30%, more particularly 5-20%, by weight based on the total weight of said perfume composition.

The perfume compositions described above, exhibit the odour characteristics of cyclohexal, but the perfume compositions need not be limited only to these ingredients. The perfume compositions may contain one or more additional fragrance ingredients.

Particular perfume ingredients that may be used harmoniously with the compound of the formula (I) include:

Natural ingredients, such as those selected from Iris, Mimosa, Ylang, Bergamot, jasmine and rose;

Synthetic muguet fragrance ingredients such as Cyclamen aldehyde (103-95-7), Hydroxycitronellal (107-75-5), Hydroxy Citronellal diethyl acetal (7779-94-4), Lilial (80-54-6), Cyclohexal (31906-04-4), Silvial (6658-48-6), Bourgeonal (18127-01-0), Florhydral (125109-85-5), and Cyclemax (7775-00-0);

Harmonic floral ingredients of the rose type such as ethyl phenyl alcohol (60-12-8), Dimethyl phenyl ethyl carbinol (103-05-9), Citronellol (106-22-9), Rhodinol (106-22-9), Acet. DMBC (151-05-3), Geraniol (106-24-1), Nerol (106-25-2), Nerolidol (7212-44-4), Mefrosol (55066-48-3), Peomosa (19819-98-8), citronellyl iso butyrate (97-89-2), and Majantol (103694-68-4);

Harmonic floral ingredients of the freesia type such as Linalool (78-70-6), Rossitol (215231-33-7), and Coranol (83926-73-2);

Harmonic floral ingredients of the lilac type such as Alc. Cinnamic alcohol (104-54-1), propyl phenyl alcohol (122-97-4) and Terpineol (8000-41-7);

Harmonic floral ingredients of the jasmine type such as benzyl acetate (140-11-4), Hedione (24851-98-7), Hexyl Cinnamic aldehyde (101-86-0), and Amyl Cinnamic aldehyde (122-40-7);

Harmonic floral ingredients of the muguet type such as Super Muguet (26330-65-4), Hydroxycitronellal dimethyl acetate (141-92-4), Magnol (92046-49-6), Mugetanol (63767-86-2), Mugesia (56836-93-2), Indole (120-72-9), and Indolene (67860-00-8);

Green harmonic ingredients such as cis 3 Hexenol (928-96-1), phenyl acetic aldehyde (122-78-1), Maceal (67845-30-1), cis 3 hexenyl acetate (3681-71-8), Acetal CD (29895-73-6), Precarone (74499-58-4), Mefranal (55066-49-4), Elintaal (40910-49-4), Glycolierral (68901-32-6), and Coranol (83926-73-2);

Fresh harmonic ingredients such as C11 undecelenic aldehyde (112-45-8), C11 undecylic aldehyde (112-44-7), C10 aldehyde (112-31-2), C12 MNA aldehyde (110-41-8), Tropional (1205-17-0), Citral (5392-40-5), Oxyde de Limette (73018-51-6), Florhydral (125109-85-5), Floralozone (67634-15-5), Dihydro Farnesal (51513-58-7), Dihydrofarnesol (51411-24-6), Adoxal (141-13-9), Citronellyl Oxyacetaldehyde (7492-67-3), Floral super (71077-31-1) and Dodecenal (4826-62-4);

Harmonic woody ingredients such as Irisone (8013-90-9) and methyl Ionone (1335-46-2);

Harmonic powdery ingredients such as Fixolide (21145-77-7), Thibetolide (106-02-5), Heliotropine (120-57-0) and Vanilline (121-33-5); and Diverse harmonic floral ingredients such as Phixia (107-75-5), Farnesal (19317-11-4), Farnesyle acetate (29548-30-9), Rhodinyl acetate (141-11-7), Cyclomethylene Citronellol (15760-18-6), Mayol (5502-75-0), Myraldyl acetate (72403-67-9), and Melonia (3613-30-7), wherein the CAS numbers of the molecules are provided in parentheses.

In addition to the aforementioned perfume ingredients that may be employed as being particularly complimentary to the odour characteristics of the compound of formula (I), other fragrance ingredients commonly used in perfumery may be employed, for example any of those ingredients described in "Perfume and Flavour Chemicals", S. Arctander, Allured Publishing Corporation, 1994, IL, USA, which is incorporated herein by reference, including essential oils, plant extracts, absolutes, resinoids, odourants obtained from natural products and the like. However, it is preferred that the perfume compositions contain no, or substantially no, cyclohexal.

Furthermore, perfume compositions may comprise adjuvants that are commonly employed in perfumery. The term "adjuvant" refers to ingredients, which are employed in perfume compositions for reasons other than, or not specifically related to, a composition's odour characteristics. For example, an adjuvant may be an ingredient that acts as an aid to processing a perfume ingredient or ingredients, or a composition containing said ingredient(s), or it may improve handling or storage of a perfume ingredient or composition containing same. It might also be an ingredient that provides additional benefits such as imparting colour or texture. It might also be an ingredient that imparts light resistance or chemical stability to one or more ingredients contained in a perfume ingredient or mixture or composition containing same. A detailed description of the nature and type of adjuvants that can be employed in perfume mixtures or compositions containing same cannot be exhaustive, but it has to be mentioned that said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

In a particular embodiment of the present invention a composition comprising a compound of formula (I), optionally in combination with a compound of formula (II) or perfume composition containing same, as herein defined, contains an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9). More specifically, Tinogard Q in triethyl citrate (TEC) can be preferentially used as an antioxidant of 5,9-dimethyl-9-hydroxy-decen-4-al. The antioxidants may be applied in levels of 0.5 to 3% in the neat compound 5,9-dimethyl-9-hydroxy-decen-4-al.

As stated hereinabove, certain levels of compound (II) can be employed to compliment the odour characteristics of 5,9-dimethyl-9-hydroxy-decen-4-al (I). However, for reasons related to olfactive quality, the levels of compound (II) should not be too high, and preferably should not extend beyond the levels referred to hereinabove. Applicant found that unless precautions are taken to prevent excessive oxidation of 5,9-dimethyl-9-hydroxy-decen-4-al (I), undesirable levels of compound (II) can be produced. Accordingly, an anti-oxidant should be employed in combination with 5,9-dimethyl-9-hydroxy-decen-4-al (I).

Any one or more of the perfume ingredients or adjuvants employed in the present invention might be formulated in a delivery vehicle if desired to provide a desired effect. Delivery vehicles may include encapsulates. Alternatively, a delivery vehicle may be in the form of a solid support, e.g. a polymeric support material onto which one or more perfume ingredients or adjuvants may be chemically or physically bound. Still further, one or more perfume ingredients or adjuvants may be dissolved or dispersed in a matrix material, which serves to control the rate at which said ingredient or ingredients emanates therefrom. In yet an alternative embodiment, one or more ingredients or adjuvants may be supported on a porous substrate, such as a cyclodextrin or a zeolite or other inorganic material. In a still further embodiment, one or more perfume ingredients may be provided in the form of a pro-perfume, which will react in a suitable environment to release the perfume ingredient in a controlled manner.

Having regard to the foregoing, it will be appreciated that a perfume mixture or a perfume composition may be fragrance is at least partly in solid form, in gel form, in foam form and/or liquid form. If it is present in solid form, it then it may take the form of granules, powders or tablets.

The compound of formula (I), perfume mixtures or perfume compositions described herein may be employed to add a characteristic odour to all manner of articles, such as fine fragrances, personal care and household care compositions.

According to another aspect of the present invention there is provided a method of imparting a muguet odour to a composition comprising the step of adding to said composition a compound according to formula (I), a perfume mixture or a perfume composition containing said compound.

Personal and household care compositions include, but are not limited to a textile treatment product, an ironing aid, a cleaning cloth, a laundry detergent, a cleaning product, in particular, for hard and/or soft surfaces, a household cleaner, a care product, a wash care product, a laundry care product, a room fragrancer, and air freshener, a conditioner, a colorant, a fabric conditioner, a conditioning substrate, a pharmaceutical, a crop protection product, a polish, a food, a cosmetic product, a fertilizer, a building material, an adhesive, a bleach, a decalcifier, an autocare product, floorcare product, cookercare product, leathercare product or furniture care product, a scourer, a disinfectant, a fragrancer, a mold remover and/or a precursor of the aforementioned products.

The skilled person is fully aware of the applicability of perfume ingredients, mixtures and compositions to personal and house hold care compositions and a very detailed description of such compositions is not warranted here. However, specific compositions that can be mentioned include cleaning compositions; autocare compositions; Cosmetic compositions; textile treatment compositions; and Air freshener and air care compositions.

Cleaning products include:

Toilet cleaners or lavatory cleaners, in other words, products for cleaning lavatory bowls and urinals, these products being supplied preferably in the form of powders, blocks, tablets or liquids, preferably gels. Besides other typical ingredients such as surfactants, they generally include organic acids e.g., citric acid and/or lactic acid) or sodium hydrogen sulfate, amidosulfuric acid or phosphoric acid for removing limescale or urine scale;

Pipe-cleaning products or drain cleaners. These are typically strongly alkaline products which serve in general to remove pipe blockages comprising organic materials-such as hair, fat, food residues, soap deposits, and the like. Additions of Al powder or Zn powder may serve for the formation of H2 gas with an effervescence effect. Possible ingredients are commonly alkalis, alkaline salts, oxidizing agents, and neutral salts. Supply forms in powder form preferably also include sodium nitrate and sodium chloride. Pipe-cleaning products in liquid form may preferably also include hypochlorite. There are also enzyme-based drain cleaners as well. Acidic products are likewise possible;

Universal or all-purpose or general-purpose cleaners. These are cleaners which can be used universally for all hard surfaces in the household and in commerce that can be wiped down wet or damp. Generally speaking, they are neutral or slightly alkaline or slightly acidic products, especially liquid products. All-purpose or general-purpose cleaners generally contain surfactants, builders, solvents and hydrotropes, dyes, preservatives, and the like;

All-purpose cleaners with special disinfectant properties. They additionally include active antimicrobial ingredients (e.g., aldehydes, alcohols, quaternary ammonium compounds, amphoteric surfactants, triclosan);

Sanitary cleaners. These are products for cleaning in bath and toilet. The alkaline sanitary cleaners are used preferably for removing fatty soiling, whereas the acidic sanitary cleaners are employed in particular, for removing limescale. Sanitary cleaners advantageously also have a considerable disinfectant action, particularly the strongly alkaline sanitary cleaners that contain chlorine;

Oven cleaners or grill cleaners which may be supplied in the form of gels or foam sprays. They generally serve for removing burnt-on or carbonized food residues. Oven cleaners are preferably given a strongly alkaline formulation using, for example, sodium hydroxide, sodium metasilicate, 2-aminoethanol. In addition they generally contain anionic and/or nonionic surfactants, water-soluble solvents, and, in some cases, thickeners such as polycarboxylates and carboxymethylcellulose;

Metal polishes. These are cleaners for particular types of metal such as stainless steel or silver. Stainless steel cleaners preferably contain, besides acids (preferably up to 3% by weight, e.g., citric acid, lactic acid), surfactants (in particular, up to 5% by weight, preferably nonionic and/or anionic surfactants), and water, solvents as well (preferably up to 15% by weight) to remove fatty soiling, and also further compounds such as thickeners and preservatives. Very fine polishing structures are included, furthermore, in products for preferably bright stainless steel surfaces. Silver polishes, in turn, may be provided in an acidic formulation. In particular, for removing black deposits of silver sulfide they contain, preferably, complexing agents (e.g., thiourea, sodium thiosulfate). Typical supply forms are polishing cloths, dipping baths, pastes, and liquids. Dark discolorations (oxide layers) are removed using copper cleaners and nonferrous-metal cleaners (e.g., for brass and bronze). They generally have a weakly alkaline formulation (preferably with ammonia) and in general contain polishing agents and also, preferably, ammonium soaps and/or complexing agents;

Glass cleaners and window cleaners. These products serve preferably to remove dirt, especially greasy dirt, from glass surfaces. Preferably they contain compounds such as anionic and/or nonionic surfactants (in particular, up to 5% by weight), ammonia and/or ethanolamine (in particular, up to 1% by weight), ethanol and/or 2-propanol, glycol ethers (in particular, 10-30% by weight), water, preservatives, dyes, anti-misting agents and the like; and Special-purpose cleaning products, examples being those for glass-ceramic hobs, and also carpet cleaners and stain removers.

Autocare products include:

Paint preservers, paint polishes, paint cleaners, wash preservers, shampoos for auto washing, auto-wash and wax products, polishes for trim metals, protective films for trim metals, plastics cleaners, tar removers, screen cleaners, engine cleaners, and the like.

Cosmetic products include:

(a) cosmetic skincare products, especially bath products, skin washing and cleansing products, skincare products, eye makeup, lip care products, nail care products, intimate care products, foot care products;

(b) cosmetic products with specific effects, especially sunscreens, tanning products, de-pigmenting products, deodorants, antiperspirants, hair removers, shaving products, perfumes;

(c) cosmetic dental-care products, especially dental and oral care products, tooth care products, cleaners for dental prostheses, adhesives for dental prostheses; and (d) cosmetic hair care products, especially hair shampoos, hair care products, hair setting products, hair-shaping products, and hair coloring products.

Textile treatment products include:

Detergents or fabric conditioners, for example, in either liquid or solid form.

Air fresheners and room fragrancers include:

Products that contain preferably volatile and usually pleasant-smelling compounds which advantageously can even in very small amounts mask unpleasant odours. Air fresheners for living areas contain, in particular, natural and synthetic essential oils such as pine needle oils, citrus oil, eucalyptus oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants. Other presentation forms include sticks and blocks. They are produced typically using a gel concentrate comprising essential oils. It is also possible to add formaldehyde (for preservation) and chlorophyll (preferably <5% by weight), and also further ingredients. Air fresheners are not, however, restricted to living spaces, but may also be intended for autos, cupboards, dishwashers, refrigerators or shoes, and even their use in vacuum cleaners is a possibility. In the household (e.g., in cupboards), for example, in addition to the odour improvers, disinfectants as well are employed, containing preferably compounds such as calcium phosphate, talc, stearin, and essential oils, these products taking the form, for example, of sachets.

There now follows a series of examples that serve to further illustrate the invention.

EXAMPLE 1

(E/Z)-5,9-dimethyl-9-hydroxy-decen-4-al (I)

a) 2,6-dimethyloct-7-yne-2,6-diol (2)

The reactor was charged with water (1593 ml) and sulfuric acid (875 g, 8.7 mol) was added. The solution was cooled to 20° C. 3,7-dimethyloct-6-en-1-yn-3-ol (1, 2.45 kg, 16.1 mol) was added and the mixture was stirred at 25° C. for 48 hours.

Water (1.5 l) and methyl tert.-butyl ether (1.6 l) was added and the mixture was stirred for 10 minutes. The layers were separated and the aqueous layer was extracted with methyl tert.-butyl ether (1.6 l). The organic layers were combined and washed with NaOH 2M (250 ml, pH 0), with saturated KHCO3 solution (700 ml, pH 8-9) and brine (800 ml). The solution was dried over MgSO4 and concentrated in vacuo. Residual 3,7-dimethyloct-6-en-1-yn-3-ol and volatile side products were removed by distillation over a 20 cm Vigreux column (b.p. 35-104° C. at 0.4 mbar). The crude product was wipe-film distilled (150° C. at 0.06 mbar) to afford (2) (1642 g, 69% yield) as a light yellow liquid. The product will crystallize upon standing. A sample was crystallized from hexane to afford white crystals, m.p. 48-49° C.

1H NMR: 3.36 (s, 1H); 2.40 (s, 1H); 2.20 (s, 1H); 1.67-1.39 (m, 6H); 1.43 (s, 3H); 1.16 (s, 6H). 13C NMR: 88.5 (s), 71.7 (d), 71.6, 68.1 (2s), 44.2, 44.0 (2t), 30.2, 29.6, 29.5 (3q), 19.8 (t).

MS: 137 (10, M+-CH3, H2O), 109 (29), 79 (40), 77 (15), 71 (15), 69 (42), 66 (59), 59 (100), 56 (28), 43 (91), 41 (21).

b) 2,6-dimethyloct-7-ene-2,6-diol (3)

A reactor equipped with an aeration stirrer was charged with 2,6-dimethyloct-7-yne-2,6-diol (2, 2.4 kg, 14.1 mol) and toluene (1.8 l). Palladium on activated carbon poisoned with lead (Lindlar catalyst, 25 g) was added and the reactor was flushed first with inert gas and then with hydrogen. The mixture was hydrogenated at 0.1-0.2 bar for 7.5 hours until the theoretical amount of hydrogen was consumed. Throughout the reaction the temperature was kept at 34-40° C. by means of a water bath. At the end of the reaction analysis by GC showed 6% over hydrogenated side product. The catalyst was removed by filtration and the toluene solution of (3) was used for the next synthetic step without further treatment. A sample of (3) was recrystallized from hexane for spectroscopic analysis, m.p. 46-47° C.

1H NMR: 5.83 (dd, J=17.4, 10.8, 1H); 5.12 (dd, J=17.4, 1.5, 1H); 4.95 (dd, J=10.8, 1.5, 1H); 2.29 (bs, 2H); 1.49-1.25 (m, 6H); 1.2 (s, 3H); 1.12 (s, 6H). 13C NMR: 145.6 (d), 111.9 (t), 73.6, 71.3 (2s), 44.5, 43.1 (2t), 29.6, 28.0 (3q), 19.0 (t).

MS: 154 (1, M+-H2O), 121 (16), 81 (35), 71 (100), 69 (25), 68 (45), 59 (36), 56 (36), 55 (18), 43 (53), 41 (17).

c) (E/Z)-5,9-dimethyl-9-hydroxy-decen-4-al (I)

In a pressure vessel with stirrer (Büchi, 5000 ml) a mixture of 2,6-dimethyloct-7-ene-2,6-diol in toluene (3, 2.25 l, 7 mol), from the previous hydrogenation reaction, ethyl vinyl ether (1.26 kg, 17 mol) and phenyl phosphonic acid (13 g, 82 mmol) were added. The autoclave was flushed and pre-pressurized to 2 bar with nitrogen and heated to 150° C. (pressure 4-6 bar) for 30 minutes. The temperature was then raised to 175° C. (pressure 8-10 bar) and maintained for 50 minutes. The reaction mixture was cooled and transferred to a 10 l jacketed reactor. Water (3 l) and HCl (2M, 300 ml) was added and the mixture was stirred at 50° C. until GC analysis showed the complete hydrolysis of the acetals of (I) in the mixture. The mixture was neutralized with saturated aqueous KHCO3 solution and the layers were separated. The aqueous layer was extracted with MtBE, the organic layers were combined and washed with acetic acid (10%, 500 ml) dried over MgSO4 and concentrated in vacuo. The crude product was wipe-film distilled (150° C., 0.06 mbar) to afford (I) (1077 g, 78% yield) as a light orange liquid.

The crude material was distilled over a 50 cm, 1' diameter column with Sulzer packing (b.p. 109° C., 0.05 mbar) to afford olfactively pure (I) (514 g, 37% yield). Refractive index 1H NMR; mixture of E/Z isomers: 9.73 (t, J=1.77, 1H); 9.72 (t, J=1.77, 1H); 5.07 (t, J=7.07, 2H); 2.46-2.40 (m, 4H); 2.34-2.25 (m, 4H); 2.01 (m, 2H); 1.94 (m, 2H); 1.65 (q, J=1.27, 3H); 1.61 (bs, 2H (OH)); 1.59 (bs, 3H); 1.48-1.32 (m, 8H); 1.18 (s, 6H); 1.17 (s, 6H). 13C NMR; mixture of E/Z isomers: 203.0, 202.9 (2d), 137.3, 137.2 (2s), 123.2, 122.5 (2d), 71.2, 71.1 (2s), 44.5, 44.3, 44.0, 43.7, 40.3, 32.4 (6t), 29.6 (4q), 23.6 (q), 23.0, 22.9, 21.2, 21.0 (4t), 16.3 (q).

MS; sum of E/Z isomers: 180 (1, M+-H2O), 96 (33), 93 (27), 81 (82), 69 (44), 68 (55), 67 (39), 59 (100), 55 (55), 43 (64), 41 (59).

Odour: floral, green, muguet, hydroxy citronellal aspect

The reported NMR spectra were measured in CDCl3 at 400 MHz if not otherwise stated; chemical shifts are reported in ppm downfield from TMS; coupling constants J in Hz. The GC/MS analyses were run using a ZB-5 column, if not stated otherwise. All purified products were either crystallized and isolated as white solids or purified by distillation in vacuo and isolated as colorless oils, the purity was confirmed by GC/MS. Samples for olfactory evaluation were purified by rectification over a distillation column with Sulzer packing.

EXAMPLE 2

In this example, the methodology of Example 27 of GB 981,702 was followed and the product isolated and characterised.

Crystalline hydroxy linalool (171 g, 0.993 mol, m.p. 46-47° C.) was dissolved in ethyl vinyl ether (240 g, 3.325 mol) and placed in a PARR autoclave. Phosphoric acid (0.6 g) was added and the mixture was heated at 180° C. for 30 minutes. The mixture was cooled to room temperature, neutralized with triethylamine (2.4 ml) and concentrated in vacuo (100° C., 14 mm). The residue (205.6 g) was added to a mixture of sodium sulfite (500 g) and water (2000 ml) and stirred for 1 hour. The pH was set to 7 by adding acetic acid (2 g) and the mixture was then extracted with MtBE three times. The combined ether extracts were concentrated in vacuo to afford the non-aldehydic constituents (90.6 g) In the patent the inventors reported 44 g of non-aldehydic material. The aqueous layer was treated with NaOH 30% (1000 ml) while cooling the mixture with an ice/water bath. The mixture (pH 14) was then extracted three times with MtBE, the organic layers were combined, washed with sodium bicarbonate solution and concentrated. The dark viscous residue (91.3 g), in the patent the inventors reported 182 g, was dissolved in acetone (500 ml) and 10% sulfuric acid (200 ml) was added. The mixture was left standing over night. The mixture was then diluted with water (2000 ml) and extracted five times with MtBE. The combined ether extracts were washed with sodium bicarbonate and concentrated in vacuo. The crude material was purified by distillation (bp. 85° C., 0.5 mbar) to afford a equally distributed mixture of (E/Z)-5,9-dimethyldeca-4,8-dienal and (E/Z)-5, 9-dimethyldeca-4,9-dienal (5.66 g, 3.16% yield). Refractive index: $n_D^{20}$ 1.4682

Odour: Fruity, apple, citrus, fatty, aldehydic, metallic, slightly hot iron, long lasting 1H NMR; mixture isomers: 9.76 (q, J=1.77, 4H); 5.14-5.04 (m, 6H); 4.69 (m, 4H); 2.45 (m, 8H); 2.33 (m, 8H);

2.11-1.93 (m, 16H); 1.74-1.66 (m, 18H); 1.64-1.59 (m, 12H); 1.57-1.47 (m, 4H). 13C NMR; mixture of isomers: 202.92, 202.85, 202.83, 202.79 (4d), 146.23, 146.07 (2s), 137.41, 137.29, 137.21 (4s), 132.11, 131.83 (2s), 124.47, 124.42, 123.21, 123.18, 122.48, 122.40 (6d), 110.27, 110.20 (2t), 44.55, 44.35, 44.32, 39.99, 39.54, 37.98, 37.69, 32.29, 31.75, 26.95, 26.80, 26.23, 26.19 (14t), 26.07, 26.03, 23.70, 23.69, 22.76 (6q), 21.24, 21.21, 21.07, 21.03 (4t), 18.04, 18.00, 16.40, 16.31 (4q).

MS 5,9-dimethyldeca-4,9-dienal; sum of E/Z isomers: 180 (1, M$^+$-H$_2$O), 96 (55), 81 (100), 79 (34), 69 (41), 68 (97), 67 (66), 55 (95), 53 (35), 41 (95), 39 (37).

MS 5,9-dimethyldeca-4,8-dienal; sum of E/Z isomers: 180 (1, M$^+$-H$_2$O), 137 (1), 136 (1), 93 (14), 69 (100), 67 (11), 55 (24), 53 (11), 43 (1), 41 (66), 39 (11).

EXAMPLE 3

To a 1000 mL multi-necked flask fitted with stirrer, condenser and dropping funnel is charged a solution of 180 g hydroxylinalool in 180 g toluene; 0.9 g phosphoric acid (85%); and 0.3 g triethanolamine. The flask is heated to 125° C. with stirring, and 150 g diethyleneglycol divinylether is added over 2 hours, and the mixture stirred whilst maintaining this temperature. After addition, 10 g of toluene is added to the flask and the mixture is stirred for a further 2.5 hours at the same temperature. Thereafter, the reaction mixture is washed 3 times at 70° C. with a solution of 10 g sodium chloride in 120 g water. After washing with 10% aqueous solution of Sodium bicarbonate and water, toluene is distilled off and the residue fractionated in vacuo to yield (E&Z)-9-hydroxy-5,9-dimethyldec-4-enal as a colorless to pale yellow oil.

EXAMPLE 4

Sodium metabisulphite (9.59 g) was dissolved in water and 9-hydroxy-5,9-dimethyldec-4-enal (10 g) was added thereto. Ethanol (10 ml) was added to the solution and the mixture became turbid. The mixture was stirred for 30 minutes at room temperature. GC analysis of the organic material showed that almost all aldehyde was in the water phase in the form of its sulphonate adduct. The mixture was stirred for a further 30 minutes before adding 50 ml of MtBE. The layers were separated and the aqueous layer was extracted another 2 times with 10 ml MtBE. The pH of the aqueous phase was 4.4. A portion was taken, freeze dried and subjected to analysis:

1H NMR (MeOD); mixture of E/Z isomers: ⏃ 5.19 (t, J=7.09, 2H); 4.25 (m, 2H); 2.32-1.94 (m, 10H); 1.77 (m, 2H); 1.71 (s, 3H); 1.65 (s, 3H); 1.46 (m, 8H); 1.18 (s, 12H). 13C NMR (MeOD); mixture of E/Z isomers: ⏃ 136.0, 135.8 (2s), 124.0, 123.3 (2d), 83.4 (2d), 70.1 (2s), 43.1, 43.0, 39.9, 31.7, 31.4 (6t), 27.8 (4q), 23.7, 22.4, 22.3 (4t), 22.2, 14.66 (2q). mp>84° C. decomposition.

Thereafter, to the remaining sample, sodium carbonate 15% in water was added in portions. An evolution of gas indicated that the sulphonate had decomposed. The pH was 7.1. More sodium carbonate was added in portions until the mixture reached a pH of 9.45, before the mixture was warmed to 40° C. for 30 minutes. The slightly basic aqueous solution was worked up by extraction with MtBE, and the organic phases were combined, washed with 10% acetic acid, dried and concentrated to yield 9-hydroxy-5,9-dimethyldec-4-enal once again.

EXAMPLE 5

| | INGREDIENT/% | | | |
|---|---|---|---|---|
| | Cpd (I) | FLOROSA ™ | DUPICAL ™ | PEONILE ™ |
| PERFUME COMPOSITION 1 | 80 | 20 | | |
| PERFUME COMPOSITION 2 | 80 | 19.99 | 0.01 | |
| PERFUME COMPOSITION 3 | 80 | 19.90 | | 0.1 |

Application in Fine Fragrance

Two fine fragrances, one male-type and one female-type containing cyclohexal were used as comparative formulations.

Both the male-type and the female-type fragrances were modified by removing cyclohexal and replacing it with equal amounts of the perfume compositions set forth in the above table to provide three modified male-type fragrances and three modified female-type fragrances.

The modified fragrances and the comparative formulations were each placed on a blotter. The odour characteristics of the modified fragrances and the comparative formulations were assessed by a panel of trained perfumers immediately and after 4 hours evaporation.

All modified fragrances were assessed to have remarkably similar odour characteristics as the comparative formulations, demonstrating the perfume formulae set forth in the table are suitable as replacers for cyclohexal in a fine perfumery setting.

Application in Fabric Softener

An unperfumed fabric softener base was perfumed with cyclohexal to form a comparative formulation and with similar quantities each of the perfume compositions set forth in the above table to produce test formulations. The perfumed fabric softener compositions were diluted in water and the odour characteristics of these diluted compositions were assessed by a panel of trained perfumers.

From the panel assessment it was found that the tests formulations exhibited remarkably similar odour characteristics to the comparative formulation, demonstrating the perfume formulae set forth in the table are suitable as replacers for cyclohexal in a fabric softener setting.

Application in Shower Gel

An unperfumed shower gel base was perfumed with cyclohexal to form a comparative formulation and with similar quantities each of the perfume compositions set forth in the above table to produce test formulations. The perfumed shower gel compositions were diluted in water and the odour characteristics of these diluted compositions were assessed by a panel of trained perfumers.

From the panel assessment it was found that the tests formulations exhibited remarkably similar odour characteristics to the comparative formulation, demonstrating the perfume formulae set forth in the table are suitable as replacers for cyclohexal in a shower gel setting.

Application in Shampoo

An unperfumed shampoo base was perfumed with cyclohexal to form a comparative formulation and with similar quantities each of the perfume compositions set forth in the above table to produce test formulations. The thus perfumed shampoo compositions were diluted in water and the odour characteristics of these diluted compositions were assessed by a panel of trained perfumers.

From the panel assessment it was found that the tests formulations exhibited remarkably similar odour characteristics to the comparative formulation, demonstrating the perfume formulae set forth in the table are suitable as replacers for cyclohexal in a shampoo setting.

EXAMPLE 6

In the following perfume formulation 5,9-dimethyl-9-hydroxy-decen-4-al or the mixture described in Example 5, and cyclohexal (Lyra)™ are interchangeable ingredients. 5,9-Dimethyl-9-hydroxy-decen-4-al adds, like cyclohexal, to the body, diffusivity and radiance of the fragrance composition.

| | | |
|---|---|---|
| NIRVANOLIDE | 329925-33-9 | 15.00 |
| DIPROPYLENE GLYCOL | 25265-71-8 1 | 3.96 |
| CEPIONATE | 24851-98-7 | 13.00 |
| BENZYL SALICYLATE | 118-58-1 | 10.00 |
| SERENOLIDE | 477218-42-1 | 9.00 |
| FLORYMOSS | 681433-04-5 | 9.00 |
| GEORGYWOOD | 185429-83-8 | 7.50 |
| ISORALDEINE CETONE ALPHA | 1335-46-2 | 4.50 |
| TROPIONAL | 1205-17-0 | 3.50 |
| FLORHYDRAL | 125109-85-5 | 1.00 |
| ISOEUGENOL ACETATE CRYSTAL | 93-29-8 | 0.90 |
| CASHMERAN | 33704-61-9 | 0.90 |
| DECALACTONE GAMMA | 706-14-9 | 0.35 |
| PEACH PURE | 104-67-6 | 0.30 |
| NEOCASPIRENE EXTRA | 89079-92-5 | 0.25 |
| INDOLENE 50%/CASTOR OIL | | 0.20 |
| AMBROFIX | 6790-58-5 | 0.20 |
| ETHYL VANILLIN | 121-32-4 | 0.15 |
| CYCLAL C | 68039-49-6 | 0.14 |
| DAMASCONE ALPHA | 24720-09-0 | 0.09 |
| FILBERTONE 10%/TEC | | 0.04 |
| OXANE 50%/TEC | | 0.02 |
| 5, 9-Dimethyl-9-hydroxy-decen-4-al-- | | 10.00 |
| | | 100.00 |

EXAMPLE 7

In the following perfume formulation 5,9-dimethyl-9-hydroxy-decen-4-al or the mixture described in Example 5, and cyclohexal (Lyral™) are interchangeable ingredients. 5,9-Dimethyl-9-hydroxy-decen-4-al adds, like cyclohexal, to the body, diffusivity and radiance of the fragrance composition

| | | |
|---|---|---|
| AMBROFIX | 6790-58-5 | 0.20 |
| BENZYL SALICYLATE | 118-58-1 | 10.00 |
| CASHMERAN | 33704-61-9 | 0.90 |
| CEPIONATE | 24851-98-7 | 13.00 |
| CYCLAL C | 68039-49-6 | 0.14 |
| DAMASCONE ALPHA | 24720-09-0 | 0.09 |
| DECALACTONE GAMMA | 706-14-9 | 0.35 |
| DIPROPYLENE GLYCOL | 25265-71-8 | 13.96 |
| ETHYL VANILLIN | 121-32-4 | 0.15 |
| FILBERTONE 10%/TEC | | 0.04 |
| FLORHYDRAL | 125109-85-5 | 1.00 |
| FLORYMOSS | 681433-04-5 | 9.00 |
| GEORGYWOOD | 185429-83-8 | 7.50 |
| INDOLENE 50%/CASTOR OIL | | 0.20 |
| ISOEUGENOL ACETATE CRYSTAL | 93-29-8 | 0.90 |
| ISORALDEINE CETONE ALPHA | 1335-46-2 | 4.50 |
| NEOCASPIRENE EXTRA | 89079-92-5 | 0.25 |
| NIRVANOLIDE | 329925-33-9 | 15.00 |
| OXANE 50%/TEC | | 0.02 |

-continued

| | | |
|---|---|---|
| PEACH PURE | 104-67-6 | 0.30 |
| SERENOLIDE | 477218-42-1 | 9.00 |
| 5, 9-Dimethyl-9-hydroxy-decen-4-al-- | | 10.00 |
| TROPIONAL | 1205-17-0 | 3.50 |
| | | 100.00 |

The invention claimed is:

1. A personal care composition, a household care composition or a fine fragrance composition comprising the compound 5, 9-dimethyl-9-hydroxy-decen-4-al, having the formula (I)

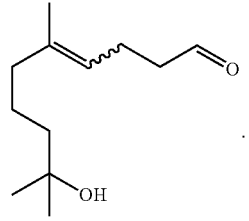

2. A personal care composition, a household care composition or a fine fragrance composition compounds according to formula (I) of claim 1, present in an E/Z isomer ratio of from 8:2 to 2:8.

3. A personal care composition, a household care composition or a fine fragrance composition comprising compounds according to claim 2, wherein the said personal care composition, a household care composition or a fine fragrance composition is free of cyclohexal.

4. A personal care composition, a household care composition or a fine fragrance composition according to claim 2, further comprising at least one adjuvant.

5. A personal care composition, a household care composition or a fine fragrance composition according to claim 4, wherein the at least one adjuvant is an anti-oxidant.

6. A method of imparting a muget odor note to a personal care composition, a household care composition or a fine fragrance composition, the method comprising the step of:
adding to or including within the personal care composition, a household care composition or a fine fragrance composition compounds according to claim 2.

7. A personal care composition, a household care composition or a fine fragrance composition according to claim 1 further comprising one or more additional compounds selected from the group consisting of: 2-cyclohexylidene-2-phenylacetonitrile; 4-(octahydro-4,7-methano-5H-inden-5-ylidene)butanal; 4-Methyl-2-(2-methyl propyl)tetrahydro-2H-pyran-4-ol; and methyl 2-(2-hexyl-3-oxocyclopentyl) acetate.

8. A personal care composition, a household care composition or a fine fragrance composition according to claim 7 wherein 2-cyclohexylidene-2-phenylacetonitrile is present in 0.001 to 10 parts by weight per 1 part by weight 5, 9-dimethyl-9-hydroxy-decen-4-al.

9. A personal care composition, a household care composition or a fine fragrance composition according to claim 7 wherein 4-methyl-2-(2-methylpropyl)tetrahydro-2H-pyran-4-ol is employed in 0.001 to 20 parts by weight per 1 part by weight 5, 9-dimethyl-9-hydroxy-decen-4-al.

10. A personal care composition, a household care composition or a fine fragrance composition according to claim 7 wherein 4-(octahydro-4,7-methano-5H-inden-5-ylidene) butanal, is employed in 0.0001 to 0.5 parts by weight per 1 part by weight 5, 9-dimethyl-9-hydroxy-decen-4-al.

11. A personal care composition, a household care composition or a fine fragrance composition according to claim 7 wherein the 5, 9-dimethyl-9-hydroxy-decen-4-al compound is present in said perfume composition in an amount of 1 to 30% by weight based on the total weight of any of the said personal care composition, a household care composition or a fine fragrance composition.

12. A personal care composition, a household care composition or a fine fragrance composition according to claim 7 wherein methyl 2-(2-hexyl-3-oxocyclopentyl)acetate is present in an amount of 0.001 to 10 parts by weight per 1 part by weight of 5, 9-dimethyl-9-hydroxy-decen-4-al.

13. A personal care composition, a household care composition or a fine fragrance composition according to claim 1, further comprising at least one perfume ingredient.

14. A personal care composition, a household care composition or a fine fragrance composition according to claim 13, wherein said at least one perfume ingredient is not cyclohexal.

15. A personal care composition, a household care composition or a fine fragrance composition comprising a compound according to formula (I) of claim 1, wherein the said composition is free of cyclohexal.

16. A personal care composition, a household care composition or a fine fragrance composition according to claim 1, further comprising at least one adjuvant.

17. A personal care composition, a household care composition or a fine fragrance composition according to claim 16, wherein the at least one adjuvant is an anti-oxidant.

18. A process of forming a personal care composition, a household care composition or a fine fragrance composition, said process comprising the steps of:
  I) reacting hydroxylinalool with ethyl vinyl ether in acid under an inert gas atmosphere at 1 to 100 bar, and a temperature of (−) 10 to 200 degrees centigrade, to form a reaction mixture comprising acetals;
  II) acidifying the cooled reaction mixture at (−20) to 40 degrees centigrade and atmospheric pressure to hydrolyse said acetals;
  III) neutralising the reaction mixture in a base before adjusting the pH of the reaction mixture to a slightly acidic pH of 2 to 7, to yield 5, 9-dimethyl-9-hydroxy-decen-4-al (I); and optionally
  IV) distilling the reaction mixture to isolate 5, 9-dimethyl-9-hydroxy-decen-4-al; and,
  V) incorporating the isolated 5, 9-dimethyl-9-hydroxy-decen-4-al within the personal care composition, or the household care composition or the fine fragrance composition.

19. A method of imparting a muget odor note to a personal care composition, a household care composition or a fine fragrance composition, the method comprising the step of:
  adding to or including within the personal care composition, a household care composition or a fine fragrance composition a compound according to formula (I) of claim 1.

* * * * *